(12) United States Patent
Dell et al.

(10) Patent No.: US 6,870,175 B2
(45) Date of Patent: Mar. 22, 2005

(54) DELIVERY METHODS, SYSTEMS AND COMPONENTS FOR USE WITH RADIOPHARMACEUTICAL SUBSTANCES

(75) Inventors: Mary Anne Dell, Pittsburgh, PA (US); Erik Witt, Mahwah, NJ (US)

(73) Assignee: Capintec, Inc., Ramsey, NJ (US)

( * ) Notice: Subject to any disclaimer, the term of this patent is extended or adjusted under 35 U.S.C. 154(b) by 184 days.

(21) Appl. No.: 10/357,277

(22) Filed: Feb. 3, 2003

(65) Prior Publication Data

US 2003/0216609 A1 Nov. 20, 2003

Related U.S. Application Data

(62) Division of application No. 10/185,290, filed on Jun. 27, 2002, now abandoned.
(60) Provisional application No. 60/301,962, filed on Jun. 29, 2001.

(51) Int. Cl.[7] .............................. G21F 5/00; A61D 7/00
(52) U.S. Cl. ............................... 250/506.1; 250/505.1; 250/507.1; 250/515.1
(58) Field of Search ......................... 250/506.1, 505.1, 250/507.1, 515.1

(56) References Cited

U.S. PATENT DOCUMENTS

| | | | | |
|---|---|---|---|---|
| 5,536,945 A | * | 7/1996 | Reich | 250/507.1 |
| 6,586,758 B2 | * | 7/2003 | Martin | 250/515.1 |
| 6,767,319 B2 | * | 7/2004 | Reilly et al. | 600/5 |
| 2003/0146399 A1 | * | 8/2003 | Martin et al. | 250/515.1 |

* cited by examiner

*Primary Examiner*—Nikita Wells
(74) *Attorney, Agent, or Firm*—Martin Fleit; Paul D. Bianco; Fleit Kain Gibbons Gutman Bongini & Bianco P.L.

(57) ABSTRACT

A method and apparatus of dispensing a radiopharmaceutical wherein a source of flushing fluid is connected to a first port of a fluid delivery set; a pressurizing unit of a powered injector system (including a powered injector and the pressurizing unit) is connected to a second port of the fluid delivery set; air is purged from the fluid delivery set; and, after purging air from the fluid delivery set, a third port of the fluid delivery set is connected to a source of the radiopharmaceutical. A valve system is included to control flow of fluid. A syringe is operatively connected with a powered injector. A radioactive shield encloses the syringe during operation to protect personnel from detrimental effects. A dose calibrator measure the radioactivity in the syringe.

1 Claim, 9 Drawing Sheets

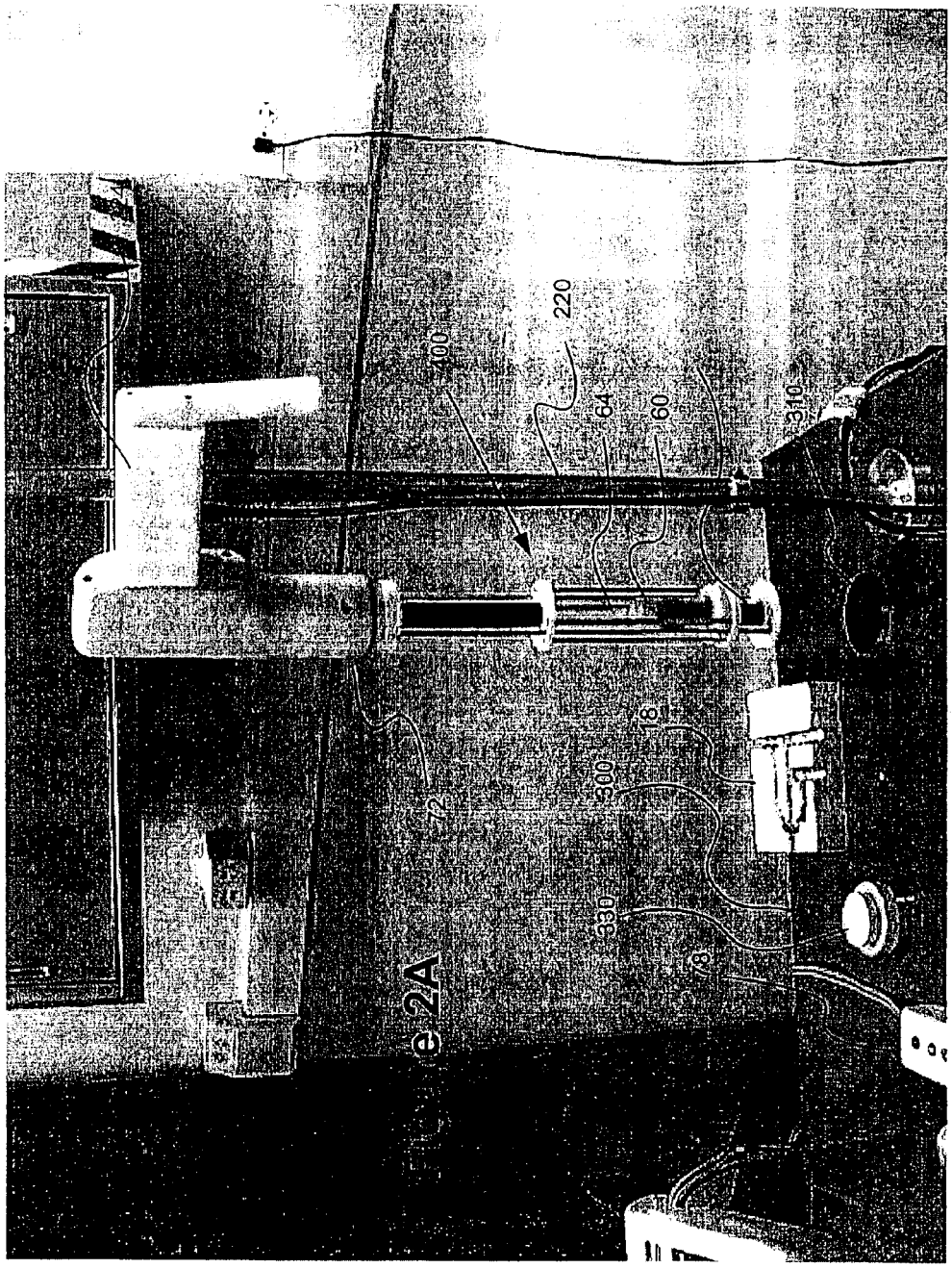

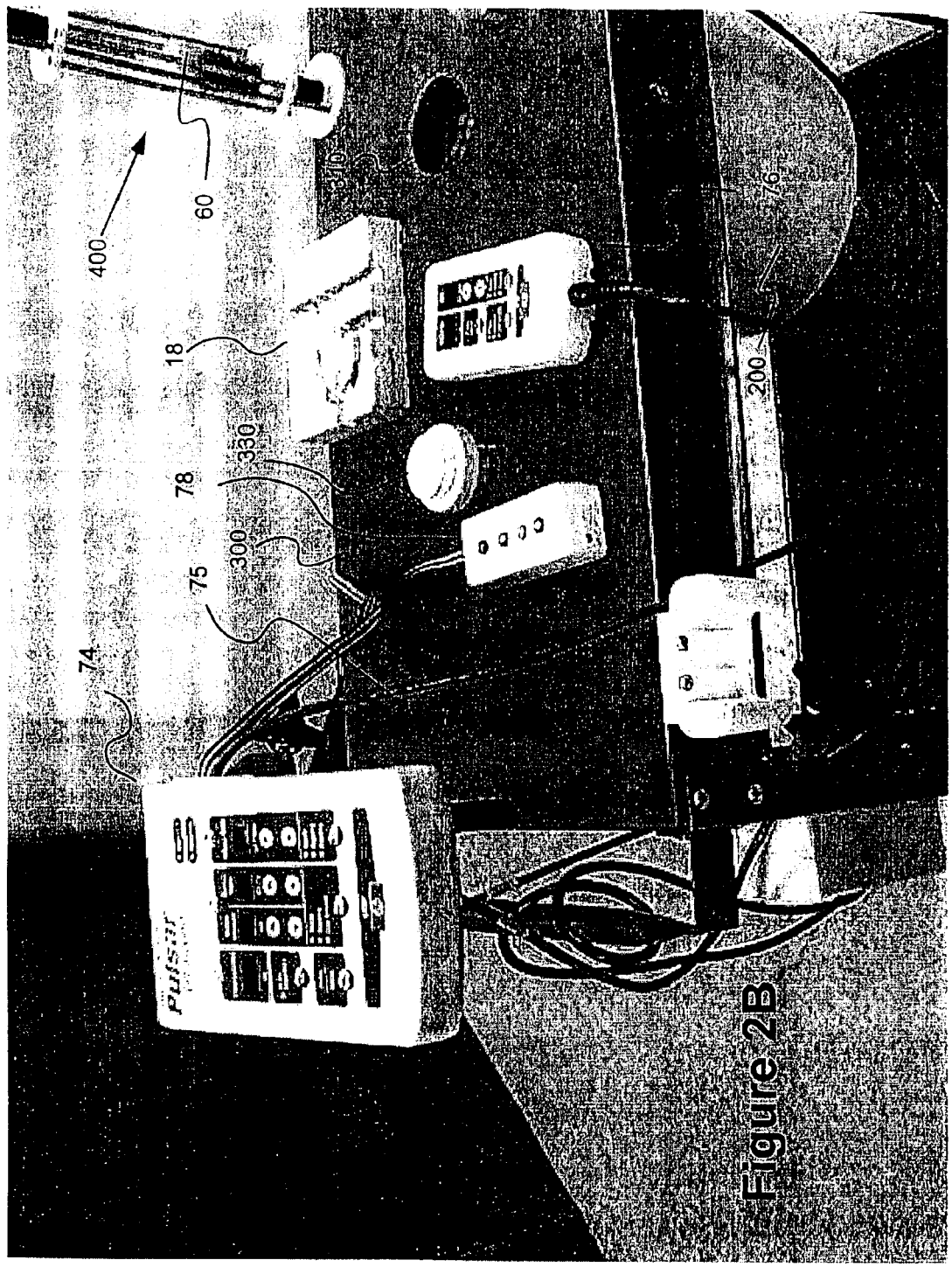

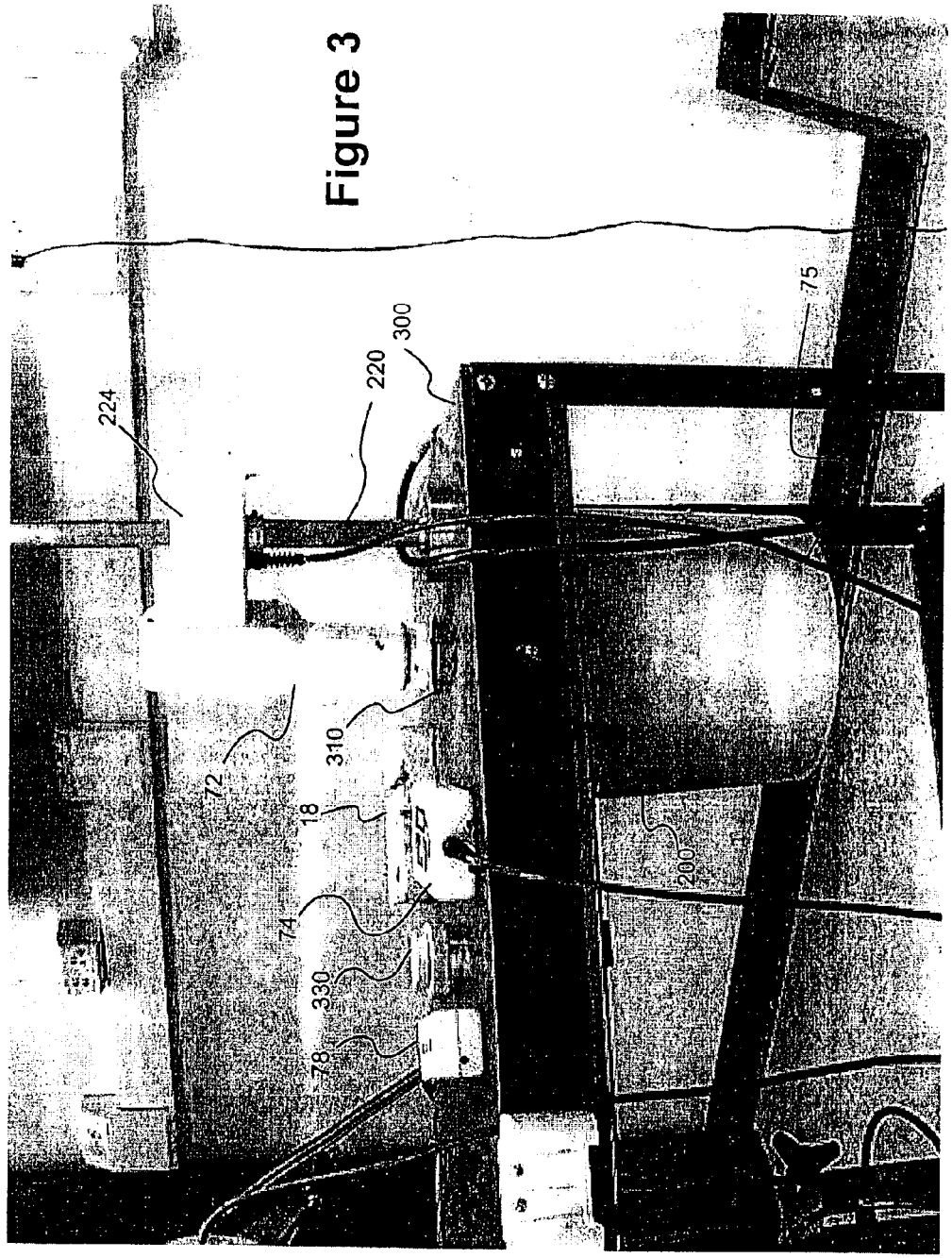

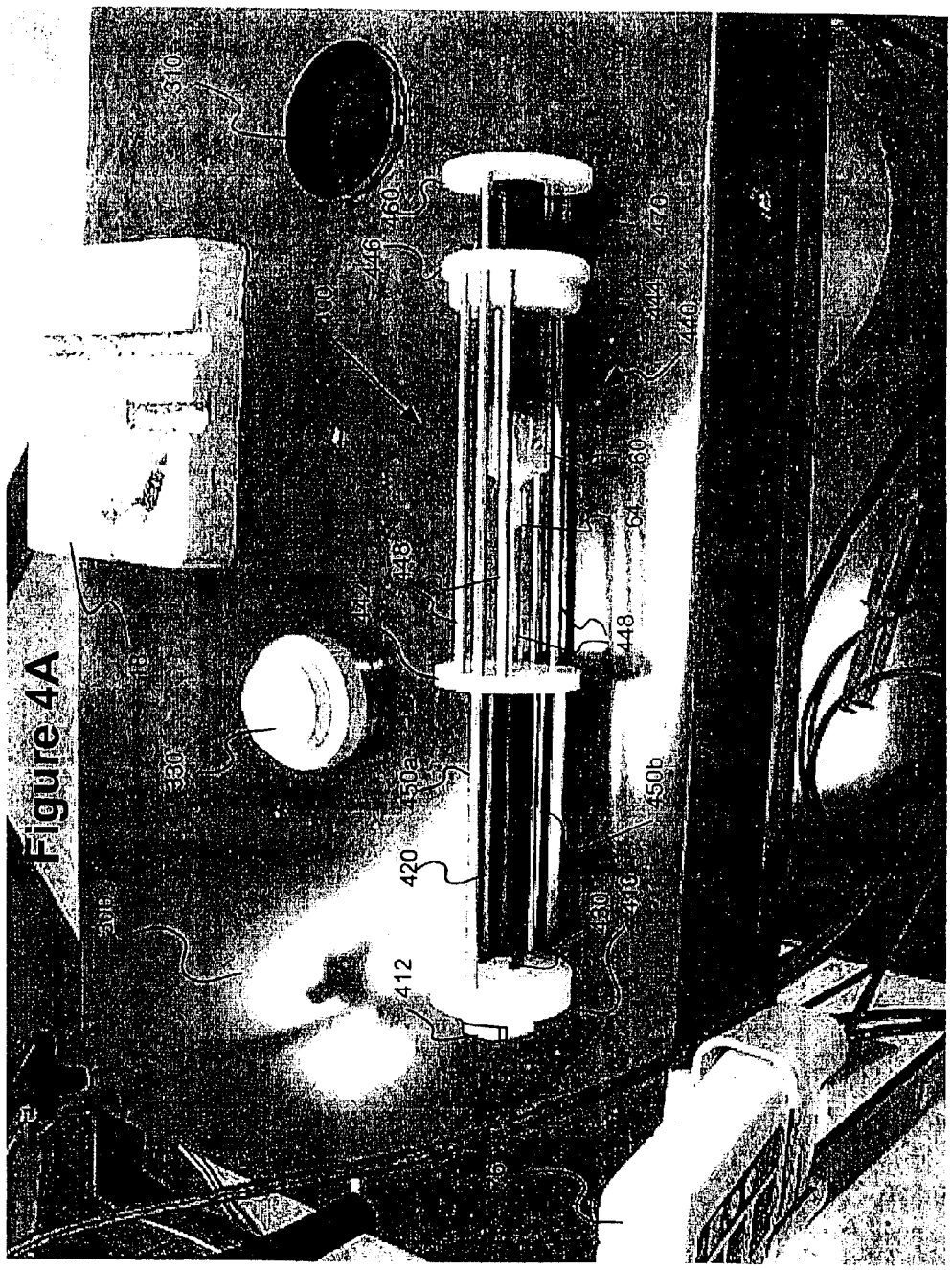

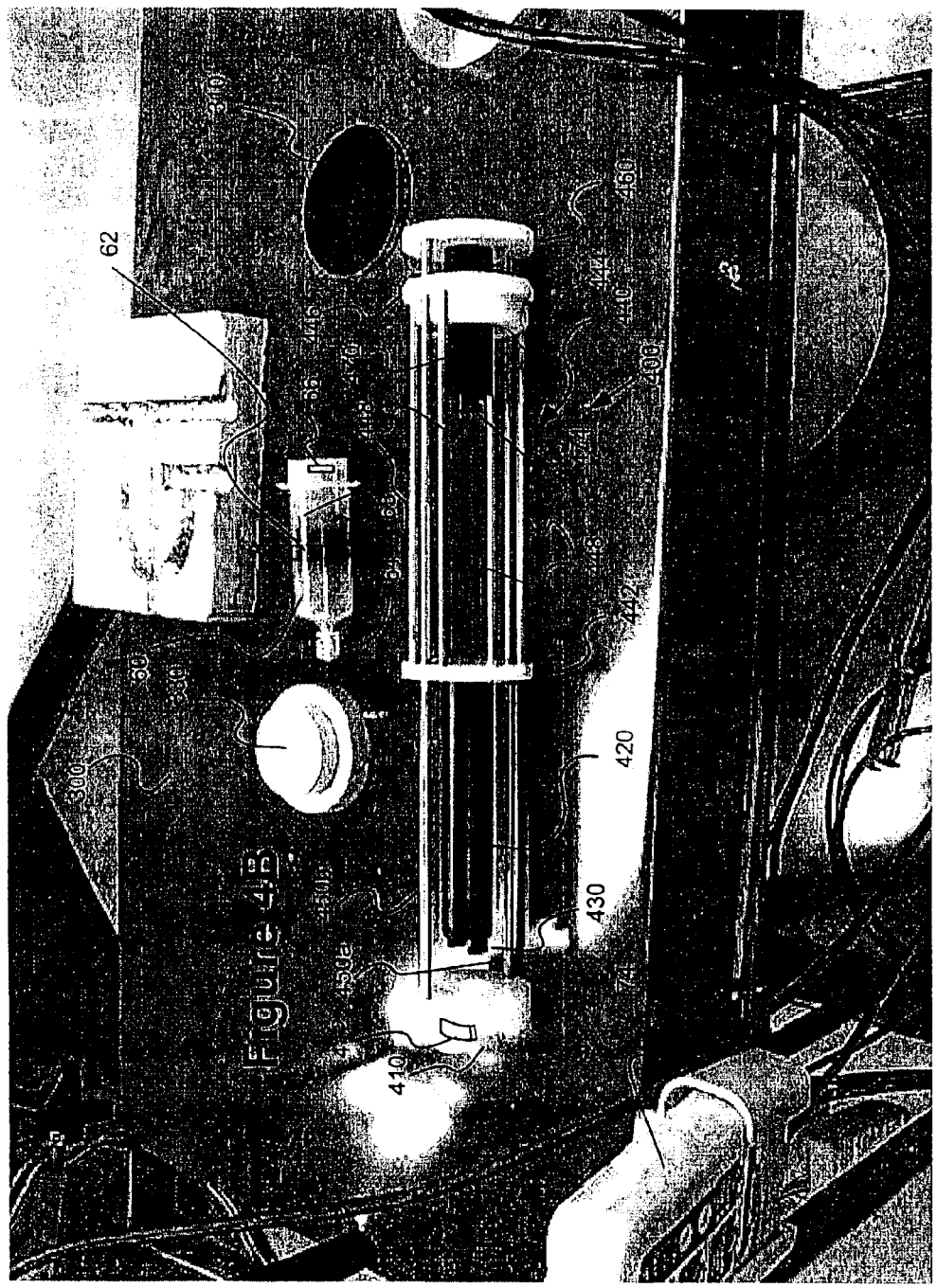

DELIVERY METHODS, SYSTEMS AND COMPONENTS FOR USE WITH RADIOPHARMACEUTICAL SUBSTANCES

CROSS REFERENCE TO RELATED APPLICATION

This application is a divisional of earlier filed U.S. application Ser. No. 10/185,290 filed Jun. 27, 2002 now abandoned, the contents of which are incorporated herein by reference; which earlier filed application claims the benefit of U.S. Provisional Application Ser. No. 60/301,962, filed on Jun. 29, 2001, the contents of which are incorporated herein by reference.

BACKGROUND OF THE INVENTION

1. Field of the Invention

The present invention dates to delivery methods, systems and components thereof for use with hazardous or toxic pharmaceutical substances, and especially to delivery and injection methods, systems and components thereof for use with radiopharmaceutical substances.

2. Prior Art

As used herein, the term "pharmaceutical" refers to any substance to be injected or otherwise delivered, into the body (either human or animal) in a medical procedure and includes, but is not limited to, substances used in imaging procedures (for example, contrast media) and therapeutic substances. A number of such pharmaceutical substances pose a danger to both the patient and the personnel administering the substance if not handled and/or injected properly. Examples of hazardous pharmaceuticals include, but are not limited to, radiopharmaceuticals, biological pharmaceuticals, chemotherapeutic pharmaceuticals and gene therapeutic pharmaceuticals.

Examples of use of a radiopharmaceutical include positron emission tomography (PET) and single-photon emission computerized tomography (SPECT), which are noninvasive, three-dimensional, imaging procedures that provide information regarding physiological and biochemical processes in patients. The first step in producing PET images or SPECT images of, for example, the brain or another organ, is to inject the patient with a dose of the radiopharmaceutical. The radiopharmaceutical is generally a radioactive substance that can be absorbed by certain cells in the brain or other organ, concentrating it there. For example, fluorodeoxyglucose (FDG) is a normal molecule of glucose, the basic energy fuel of cells, attached a radionuclide or radioactive fluor. The radionuclide is produced in a cyclotron equipped with a unit to synthesize the FDG molecule.

Cells (for example, in the brain) which are more active in a given period of time after an injection of FDG, will absorb more FDG because they have a higher metabolism and require more energy. The radionuclide in the FDG molecule suffers a radioactive decay, emitting a positron. When a positron collides with an electron, an annihilation occurs, liberating a burst of energy in the form of two beams of gamma rays in opposite directions. The PET scanner detects the emitted gamma rays to compile a three dimensional image.

In that regard, after injecting the radiopharmaceutical, the patient is typically placed on a moveable bed which slides by remote control into a circular opening of the scanner referred to as the gantry. Positioned around the opening, and inside the gantry, there are several rings of radiation detectors. Each detector emits a brief pulse of light every time it is struck with a gamma ray coming from the radionuclide within the patient's body. The pulse of light is amplified, by a photomultiplier, and the information is sent to the computer which controls the apparatus.

The timing of injection is very important. After the generation of the radiopharmaceutical, a countdown begins. After a certain time, which is a function of the half-life of the radionuclide, the radiation level of the radiopharmaceutical dose falls exactly to a level required for the measurement by the scanner. In current practice, the radiation level of the radiopharmaceutical volume or dose is typically measured using a dose calibrator. Using the half-life of the radionuclide, the time that the dose should be injected to provide the desired level of radioactivity to the body is calculated. When that time is reached, the radiopharmaceutical dose is injected using a manually operated syringe.

Most PET radionuclides have short half-lives. Under proper injection procedures, these radionuclides can be safely administered to a patient in the form of a labelled substrate, ligand, drug, antibody, neurotransmitter or other compound normally processed or used by the body (for example, glucose) that acts as a tracer of specific physiological and biological processes.

Excessive radiation to technologists and other personnel working in the scanner room can pose a significant risk, however. Although the half-life of the radiopharmaceutical is rather short and the applied dosages are themselves not harmful to the patient, administering personnel are exposed each time they work with the radiopharmaceuticals and other contaminated materials under current procedures. Constant and repeated exposure over an extended period of time can be harmful.

A number of techniques used to reduce exposure include minimizing the time of exposure of personnel, maintaining distance between personnel and the source of radiation and shielding personnel from the source of radiation. In general, the radiopharmaceutical is typically delivered to a nuclear medicine facility from another facility equipped with a cyclotron in, for example, a lead-shielded container. Often, the radiopharmaceutical is manually drawn from such containers into a shielded syringe. See, for example, U.S. Pat. No. 5,927,351 disclosing a drawing station for handling radiopharmaceuticals for use in syringes. Remote injection mechanisms can also be used to maintain distance between the operator and the radiopharmaceutical. See, for example, U.S. Pat. No. 5,514,071, disclosing an apparatus for remotely administering radioactive material from a lead encapsulated syringe.

In one procedure, the radiopharmaceutical is injected into tubing that is coiled within a lead container. Typically, the shielded syringe used to inject the radiopharmaceutical is disconnected and replaced by a larger syringe, filled in most cases with saline, for injection into the body and flush. By emptying the second syringe, the radiopharmaceutical is flushed through the shielded, coiled tubing in the container and injected into the person, to be scanned. An excess volume of saline supplies a flushing function.

Although substantial effort is made to reduce exposure of administering and other personnel to harmful radiation, some exposure is experienced under current procedures. Being in the injection room longer than necessary is thus to be avoided. Moreover, the cumulative radiation exposure resulting from multiple injection procedures must be closely monitored to avoid overexposure. Indeed, personnel that administer radiopharmaceuticals are typically periodically rotated out of such duties to reduce the risk of overexposure.

In addition to the difficulties introduced by the hazardous nature of radiopharmaceuticals, the short half-lives of such radiopharmaceutical further complicate the administration a proper dosage to a patient. As discussed above, initial calibration of radioactivity is often made and the injection is then timed so that a dose of the desired level of radioactivity to the body is delivered (as calculated from the half-life of the radiopharmaceutical). See, for example, U.S. Pat. No. 4,472,403 in which a motor driven syringe is controlled to inject a quantity of a radiopharmaceutical stored in the syringe by calculating the injection quantity based upon the half-life of the radiopharmaceutical and the delay before injection.

Radiation detectors have also been placed upon syringe shields and in line with the radiopharmaceutical delivery system. For example, U.S. Pat. No. 4,401,108 discloses a syringe loading shield for use during drawing, calibration and injection of radiopharmaceuticals. The syringe shield includes a radiation detector for detecting and calibrating the radioactive dosage of the radiopharmaceutical drawn into the syringe. U.S. Pat. Nos. 4,562,829 and 4,585,009 disclose strontium-rubidium infusion systems and a dosimetry system for use therein. The infusion system includes a generator of the strontium-rubidium radiopharmaceutical in fluid connection with syringe for supplying pressurized saline. Saline pumped through the strontium-rubidium generator exits the generator either to the patient or to waste collection. Tubing in line between the generator and the patient passes in front of a dosimetry probe to count the number of disintegrations which occur. As the flow rate through the tubing is known, it is possible to measure the total activity delivered to the patient (for example, in milliCuries). Likewise, radiation measurements have been made upon blood flowing through the patient. For example, U.S. Pat. No. 4,409,966 discloses shunting of blood flow from a patient through a radiation detector.

The danger to administering personnel and other difficulties that arise from the nature of hazardous pharmaceuticals such as radiopharmaceuticals often affect the quality and safety of the injection procedure. For example, given the care that must be taken to prevent radiation overexposure (including limiting the duration of injection procedures), the concern with properly timing an injection and the need to prevent the creation of radioactive wastes, it is often difficult to properly eliminate air from all fluid paths before an injection begins.

It is thus very desirable to develop devices, systems and methods through which toxic or hazardous pharmaceuticals (far example, radiopharmaceuticals) can be administered in controlled manner to enhance their effectiveness and patient safety, while reducing exposure of administering personnel to such hazardous pharmaceuticals.

SUMMARY OF THE INVENTION

In one aspect, the present invention provides a method of injecting a hazardous pharmaceutical comprising the steps of: connecting a source of flushing fluid to a first port of a fluid delivery set; connecting a pressurizing unit of a powered injector system (including a powered injector and the pressurizing unit) to a second port of the fluid delivery set; purging air from the fluid delivery set; and, after purging air from the fluid delivery set, connecting a third port of the fluid delivery set to a source of the hazardous pharmaceutical. The fluid delivery set can, for example, include a valve system or assembly to control flow of fluid through the fluid delivery set. The ports of the fluid delivery set can, for example, include luer connectors as known in the medical arts to form a removable, secure and generally sealed connection The method preferably further includes the steps of (i) removably connecting a disposable fluid path that is connectable (via, for example, a catheter) to a patient to the fluid delivery set and (ii) purging air from the disposable fluid path before connecting the fluid delivery set to the source of hazardous pharmaceutical.

By removing air from the fluid delivery set and the patient fluid path before any connection is made to the source of hazardous pharmaceutical, exposure of administering personnel to the hazardous pharmaceutical to that point is eliminated. Connecting the fluid delivery set to the source of pharmaceutical can be automated or otherwise accomplished remotely (for example, with use of an extending or robotic arm as known in the machine and robotic arts) to prevent exposure during that connection.

The pressurizing unit can, for example, be a syringe in operative connection with the powered injector. In the case that the pressurizing unit is a syringe, the method can further include the steps of drawing hazardous pharmaceutical into the syringe and injecting the hazardous pharmaceutical through the fluid delivery set and the disposable fluid path. Using a powered injector having a control unit removed in distance or shielded from the position of the syringe, fluid delivery set and fluid path prevents exposure of operating/administering personnel to the hazardous pharmaceutical. The method preferably further includes the step of flushing the fluid delivery set and the disposable fluid path after injection using the flushing fluid (for example, saline and/or another biologically acceptable flushing agent). A powered injector can also be used with a saline syringe in a similar manner as described above to limit exposure of operating personnel to the hazardous pharmaceutical.

In the case that the hazardous pharmaceutical is a radiopharmaceutical, the method can further include the step of measuring the level or dosage of radioactivity of the radiopharmaceutical injected. Preferably, the level of radioactivity or dosage is measured very near in time or simultaneously with delivery of the radiopharmaceutical to provide an accurate measurement of the dosage delivered. For example, the level of radioactivity can be measured by positioning the syringe within a dose calibrator. The level of radioactivity can also measured by placing a radioactivity detector in operative connection with a line through which the radiopharmaceutical is dispensed or delivered.

In another aspect, the present invention provides a system for delivery of a hazardous pharmaceutical including: a syringe in operative connection with a powered injector and a protective container to enclose the syringe during operation thereof. The protective container is constructed or adapted to protect personnel from detrimental effects of the pharmaceutical. The system preferably also includes at least one source of flushing fluid; a fluid path adapted to connect to a patient; at least one source of the pharmaceutical; and a fluid delivery set. The fluid delivery set preferably includes a valve assembly to which the syringe, the source of flushing fluid, the fluid path and the source of pharmaceutical are removably connectable.

The valve assembly preferably provides flow control through the fluid delivery set such that operator contact with the fluid delivery set is not required after connection of the source of pharmaceutical to the fluid delivery set. The valve assembly also preferably provides flow control through the fluid delivery set such that the entire fluid delivery set can be purged of air with the syringe and the source of flushing fluid in fluid connection with the valve assembly before the source of pharmaceutical is connected to the fluid delivery set. In one embodiment, the valve assembly includes a bypass line in continuous fluid connection between the source of flushing fluid and the fluid path.

In the case that the pharmaceutical is a radiopharmaceutical, the protective container can, for example, be a component of a dose calibrator adapted to measure the level of radioactivity of the pharmaceutical within the syringe. In one embodiment, the syringe is connected to the powered injector via an extending adapter that preferably extends from the powered injector when connected thereto to position the syringe within the protective container.

The adapter can, for example, include an injector attachment member to attach the adapter to a powered injector and a plunger extension fixed in position relative to a powered injector. The plunger extension preferably has a plunger attachment member to attach to a plunger of the syringe. In one embodiment, the adapter also includes a syringe carriage slidably attached to the adapter. The syringe carriage includes a syringe attachment member to removably attach a syringe thereto so that a barrel of a syringe can be moved relative to a plunger thereof to control fluid flow into and out of a syringe.

The above embodiment of an adapter facilitates orientation of the syringe tip or exit of the syringe directed toward the powered injector when the syringe is attached to the syringe attachment member. This orientation can facilitate purging of air from the syringe when the syringe is placed within, for example, a dose calibrator positioned below the injector. In that regard, lead-shielded dose calibrators are often relatively large and heavy and thus often positioned most easily near the floor. Moreover, this relative positioning of the injector and dose calibrator assists in limiting exposure of operating/administering personnel by directing any waves of radiation escaping from the dose calibrator upward to the ceiling of the room. Moving the syringe barrel relative to the syringe plunger in the manner described in the above embodiment facilitates use of commercially available injectors and syringes for use therewith by eliminating the need to change/recalibrate the direction and distance the injector drive member must advance or retract to complete a desired operation.

In another aspect, the present invention provides a method of using a powered injector system to inject a radiopharmaceutical into a body including the steps of: attaching an extending adapter to the front end of the powered injector; the adapter including an injector attachment to place the adapter in operative connection with the powered injector, the adapter also including a syringe attachment to attach a syringe to the adapter to place the syringe in operative connection with the powered injector; and extending the adapter into a radiation shield. As discussed above, the radiation shield can form part of a dose calibrator to measure the radioactivity of radiopharmaceutical within the syringe. In one embodiment, the exit of the syringe is oriented upward relative to the opposite end of the syringe when the syringe is positioned within the dose calibrator to facilitate purging of air from the syringe. As discussed above, the opening through which the syringe passed to enter the dose calibrator is preferably oriented in a direction (for example, upward toward the ceiling) to decrease the likelihood of exposure of personnel to any radiation waves exiting the dose calibrator during use thereof.

In a further aspect, the present invention provides an adapter for use with a powered injector to attach a syringe to the powered injector including: an injector attachment member to attach the adapter to a powered injector and a syringe attachment member spaced from the injector attachment member by a sufficient distance to position a syringe attached to the syringe attachment member within a radiation dose calibrator. Preferably, the adapter facilitates use of commercially available injector systems with commercially available dose calibrators without the requirement of substantial and/or expensive modification thereto.

In another aspect, the present invention provides an adapter for use with a powered injector to attach a syringe to the powered injector including an injector attachment member to attach the adapter to a powered injector and a plunger extension fixed in position relative to a powered injector. The plunger extension bas a plunger attachment member to attach to a plunger of the syringe. The adapter further includes a syringe carriage slidably attached to the adapter and including a syringe attachment member to removably attach a syringe thereto so that a barrel of the syringe can be moved relative to a plunger thereof to control fluid flow into and out of the syringe. As discussed above, the syringe can be oriented with a syringe tip thereof directed toward the powered injector when attached to the syringe attachment member.

In another aspect, an adapter includes an attachment member to removably attach the adapter to a powered injector and a syringe carriage slidably attached to the attachment member. The syringe carriage includes a syringe attachment member to which a syringe can be removably attached. The adapter further includes an end member attached a fixed distance from the attachment member. The end member has a plunger extension attached to the end member and extending toward the injector. The plunger extension includes a plunger attachment member on an end thereof opposite the end attached to the end member. The syringe carriage is adapted to move a barrel of the syringe relative to a plunger of the syringe when a syringe is attached to the syringe attachment member and a plunger thereof is attached to the plunger extension member.

In another aspect, the present invention provides a shield for use with a radiopharmaceutical including a housing that is impenetrable by radioactive energy from the radiopharmaceutical. The shield also includes at least one opening in the housing through which an article containing the radiopharmaceutical which is positioned within the housing can be viewed. The opening is in visual alignment with a reflective surface in which a viewer can view a reflection of the article. The opening is positioned within the housing such that there is no direct line between the viewer and the article that is not shielded by a portion of the housing. Because radiation energy from radiopharmaceuticals travel in straight lines, the viewer is shielded from exposure to radiation.

In a further aspect, the present invention provides a method of injecting a. radiopharmaceutical into a body including the steps of positioning a pressurizing unit or device containing a first volume of the radiopharmaceutical within a dose calibrating unit adapted to measure the level of radioactivity of the radiopharmaceutical; and injecting a second volume of the radiopharmaceutical. The second volume is determined through measurement by the dose calibrating unit to provide a desired level of radioactivity. The second volume can, for example, be less than the first volume. In one embodiment, the pressurizing chamber is a syringe in fluid connection with a powered injector.

In another aspect, the present invention provides a kit for injecting a hazardous pharmaceutical into a body including:

a fluid path adapted to connect to a patient; and a fluid delivery set. The fluid delivery set includes a valve assembly to which a pressurizing unit, a source of flushing fluid, the fluid path and a source of the pharmaceutical are removably connectable. The valve assembly provides flow control through the fluid delivery set such that operator contact with the fluid delivery set is not required after connection of the source of pharmaceutical to the fluid delivery set. The valve assembly also preferably provides flow control through the fluid delivery set such that the entire fluid delivery set can be purged of air with the syringe and the source of saline in fluid connection with the valve assembly before the source of pharmaceutical is connected to the fluid delivery set.

In still a further aspect, the present invention provides a method of injecting a radiopharmaceutical into a patient comprising the steps of: connecting a powered pressurizing device that is controlled without intimate or close contact by an operator (far example, remotely controlled, automated or preprogrammed so that the operator is not within a radiation field of a dangerous level) to a valve assembly of a fluid delivery set; connecting at least one source of a flushing fluid to the valve assembly; connecting a patient fluid path to the valve assembly, the patient fluid path terminating in a patient connector; connecting a source of a ready-made (that is, prepared earlier for example, in an offsite cyclotron) radiopharmaceutical to the valve assembly; and controlling the valve assembly at least during injection of the hazardous pharmaceutical such that operator presence in the vicinity of the radiopharmaceutical is not required. In general, a dose to an individual decreases with the square of the distance from the radiation source. Thus, close operator contact with the pressurizing device, fluid delivery set and other components of the fluid delivery system is not required when the radiopharmaceutical is present in the fluid delivery system. Moreover, shielding as described above can also be used to prevent exposure. The valve assembly can also be controlled without intimate contact by an operator (for example, remotely controlled, automated or preprogrammed).

In general, the present invention provides for administration or delivery of a toxic or hazardous pharmaceuticals (for example, radiopharmaceuticals) in a controlled manner to enhance the effectiveness of the pharmaceutical and to enhance patient safety (as compared to current procedures and equipment for delivering such pharmaceuticals), while reducing exposure of administering personnel to the hazardous pharmaceuticals. In general, commercially available injector systems are readily adaptable for use in the present invention without substantial or expensive modification.

BRIEF DESCRIPTION OF THE DRAWINGS

FIG. 2A illustrates a perspective view an embodiment of an injector and a syringe adapter of the stem of the present invention.

FIG. 2B illustrates a perspective view of injector control units used in connection with the injector of the present invention.

FIG. 3 illustrates a perspective view of the system of the present invention in which the injector head and syringe adapter have been lowered so that the syringe is positioned within the dose calibration unit.

FIG. 4A illustrates a perspective view of the adapter of FIG. 2A detached from the injector with the syringe attached thereto.

FIG. 4B illustrates a perspective view of the adapter of FIG. 2A detached from the injector with the syringe detached therefrom.

DETAILED DESCRIPTION OF THE INVENTION

Figure 1A:
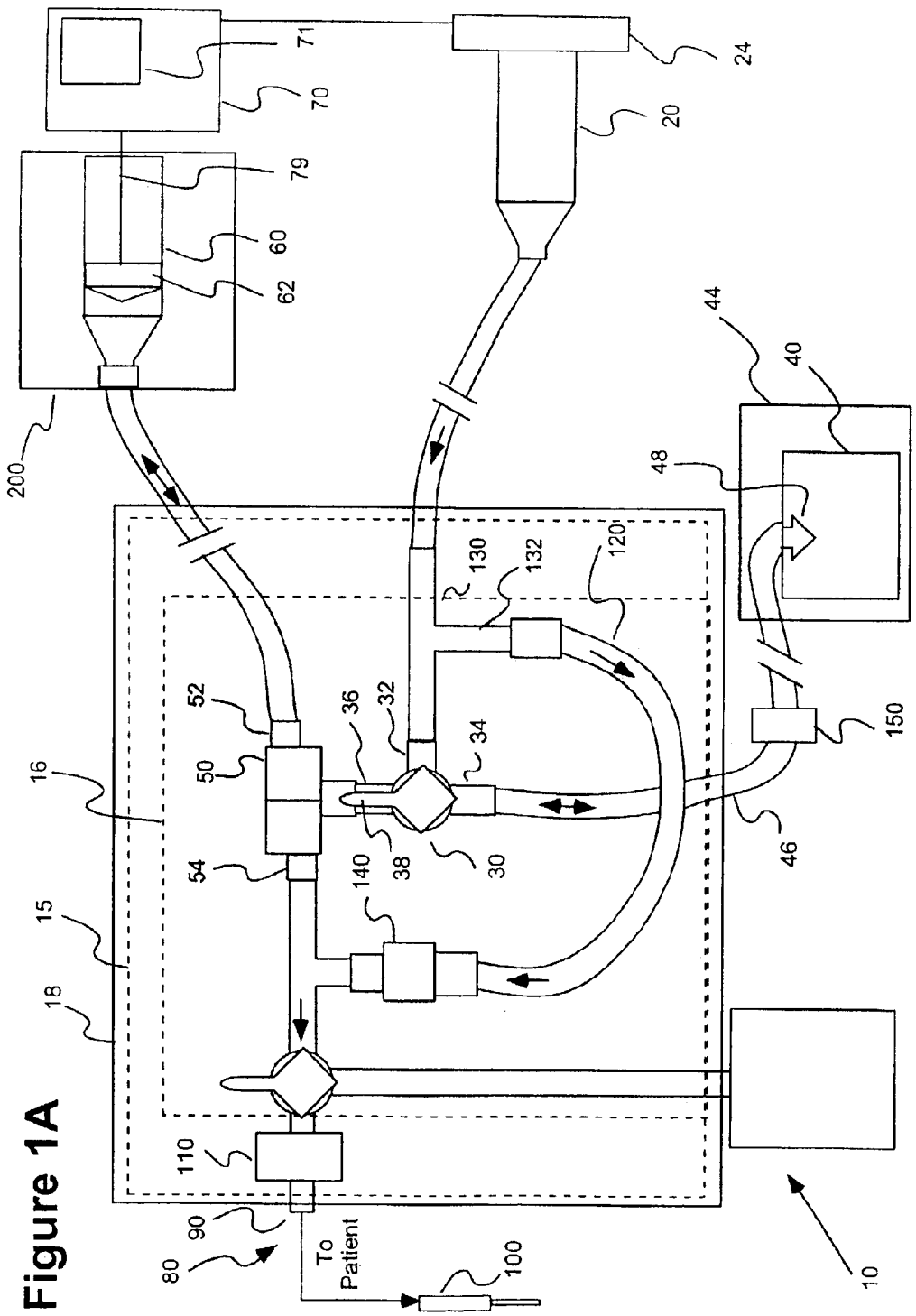
FIG. 1A illustrates a schematic representation of an embodiment of a system of the present invention.
Figure 1C:
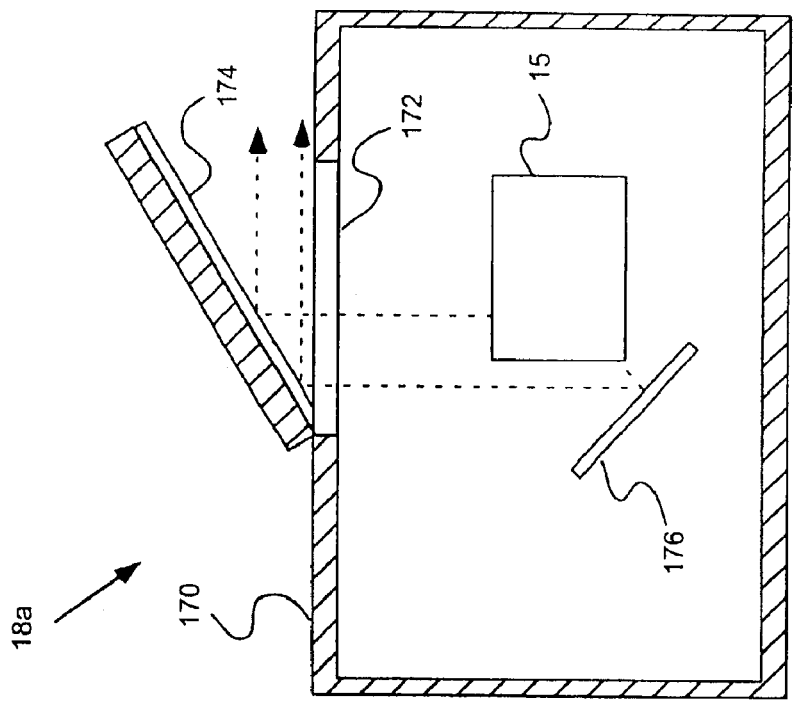
FIG. 1C illustrates a side cross-sectional view another embodiment of a shielded container for a fluid delivery set of the present invention.
Figure 1B:
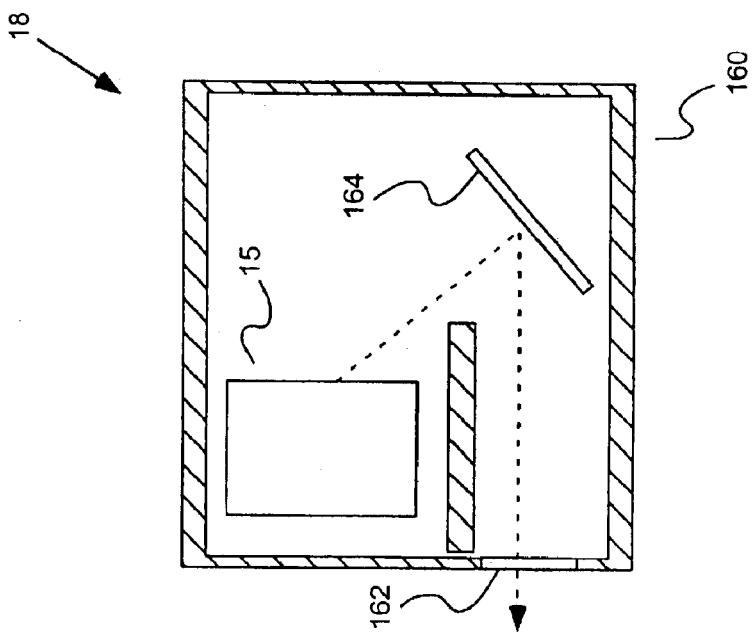
FIG. 1B illustrates a top cross-sectional view of an embodiment of a shielded container for a fluid delivery set of the present invention.

As illustrated in FIG. 1A, in one embodiment of the present invention, a system 10 includes a fluid delivery set or system 15 including a valve system 16 that provides a fluid connection for a saline source 20 (for example, a syringe), a source 40 of a pharmaceutical to be injected into a patient, a pressurizing chamber or unit for the pharmaceutical (for example, a syringe 60 in fluid connection with a powered injector 70 in the embodiment of FIG. 1) and a fluid path set 80 that is connectable to the patient (via, for example, tubing terminating in a catheter 100). In general, the fluid delivery set 16, valve system 15 and other elements of the present invention enable purging of air from the system, filling of syringe 60 with the pharmaceutical, delivery of the pharmaceutical (for example, injecting the pharmaceutical into the patient) via syringe 60, and providing a saline flush, while minimizing or eliminating exposure of administering or operating personnel to the detrimental effects of the pharmaceutical and minimizing or eliminating creation of contaminated waste. Moreover, fluid delivery set 15 and other elements of the present invention also facilitate safe delivery of the pharmaceutical to multiple destinations (for example, injection into a series patients).

In the embodiment of FIG. 1, valve system 16 includes a three-way stopcock 30 including a first port 32 that is in fluid connection with saline syringe 20. As second port 34 of stopcock 30 is in fluid connection with source 40 of a toxic or hazardous pharmaceutical (for example, a radiopharmaceutical). Source 40 of the pharmaceutical is preferably enclosed within a container 44 that is designed to reduce the risk of contamination of personnel administering the pharmaceutical. For example, in the case of a radiopharmaceutical, the container can fabricated from lead or tungsten to substantially prevent exposure of such personnel to undesirably high levels of radiation.

A third port 36 of stopcock 30 is in fluid connection with, for example, a dual check valve 50. The flow through stopcock 30 is controlled via control 38. A first port 52 of dual check valve 50 is in fluid connection with syringe 60 that is preferably in operative connection with powered injector 70. A second port 54 of dual check valve 50 its preferably in fluid connection with patient fluid path set 80 that includes, for example, flexible tubing 90 connected to catheter 100. Preferably, patient fluid path set 80 is disposable on a per patient basis to reduce the likelihood of cross-contamination when system 10 is used for injection of fluids into multiple patients. Patient fluid path set 80 is preferably in fluid connection with second port 54 of dual check valve 50 via a one-way check valve 110 to further reduce the likelihood of cross-contamination.

Preferably, saline source 20 is also in fluid connection with fluid path set 80 via bypass tubing or conduit 120 of valve system 16 to provide, for example, flush and KVO (keep vein open) functions on demand without having to adjust control 38 of valve system 15. In the embodiment of FIG. 1, a tee 130 is positioned between saline source 20 and dual check valve 30. A side port 132 of tee 130 is in fluid connection with bypass tubing 120. Bypass tubing 120 is preferably in fluid connection with check valve 110 (an thereby with fluid path set 80) via a one-way check valve 140.

In injection procedures and other fluid delivery operations in which non-hazardous pharmaceuticals are delivered, purging air from the entire fluid path (including, the fluid path between a source of the pharmaceutical and the delivery point) typically includes the forcing an amount of the pharmaceutical through the fluid path to, for example, a waste receptor before beginning the procedure (for example, before insertion of a catheter into the patient). However, in the case of a hazardous pharmaceutical such as a radiopharmaceutical, it is very desirable to minimize or eliminate the creation of waste pharmaceutical. Moreover, as discussed above, it is also preferably in, the case of a hazardous pharmaceutical to minimize exposure of administering personnel to the pharmaceutical. The present invention, thus preferably enables purging of air from the entirety of fluid delivery set 15 (and preferably, also from patient fluid path set 80) before connection of fluid delivery set 16 to pharmaceutical source 40. In this manner, exposure of administering personnel to hazardous materials during purging is eliminated and no hazardous waste is generated.

After connecting fluid delivery set 16, which is fluid filled and purged of air, to pharmaceutical source 40, air can be introduced into fluid delivery system 10 from pharmaceutical source 40. Thus, precautions are preferably taken as known in the art to reduce the likelihood of introduction of air into system 10 from pharmaceutical source 40. Moreover, a bubble detector 150 can be placed in communication with line 46 to detect if air is drawn from pharmaceutical source 40. Examples of a bubble detectors suitable for use in the present invention include the BDF/BDP series ultrasonic air bubble detectors available from Introtek of Edgewood, N.Y.

In, the case that it is desirable to purge system 10 (for example, in the case that air is found in one of the fluid path lines) a waste container 160 (which is preferably shielded) is preferably provided. In the embodiment of FIG. 1A waste container 160 is in fluid connection with a control valve 170 (similar in operation to control valve 30) which is in line just before check valve 110. Control valve 170 can be controlled remotely or automated to reduce likelihood of exposure of operating personnel to the toxic pharmaceutical. It is also possible, for example, to provide valve 50 with control in a manner known to those skilled in art such that fluid can be purged back to source 40. In general, system 10 is purged using syringe 60 and/or saline source 10 as described below.

During operation of system 10, saline syringe 20 (which can be a hand syringe or a syringe powered by an injector 24) is first filled with saline. Saline syringe 20 is then connected to valve system 16 of fluid delivery set 15 via first port 32 on three-way stopcock 30. Saline syringe 20 is preferably used to purge air from system 10. Saline syringe 20 also provides a flush to patient fluid path set 80 after injection of pharmaceutical(s) to ensure that substantially all the pharmaceutical is injected into the patient and to ensure that very little if any of the toxic or hazardous pharmaceutical remains, for example, within fluid path set 80.

Syringe 60 is attached to injector 70. In the case of injection of a radiopharmaceutical, at least syringe 60 of injector 70 is preferably enclosed within a shielded container during an injection procedure. In one embodiment, the shielded container is a radiation dose calibration unit 200 as discussed in further detail below. Air is first preferably expelled from syringe 60 by advancing plunger 62 of syringe 60 toward syringe tip 64. Syringe 60 is then connected to dual check valve 50 of valve system 16 via first port 42. Patient fluid path set 80 is connected to valve system 16 via one-way check valve 110.

Control 38 is adjusted to place saline syringe 20 in fluid connection with tubing 46. Tubing 46 can, for example, terminate in a spike 48 or other connection member to cooperate with a septum 45 on source 40 (for example, a bottle) as known in the art. A small volume of saline is injected or expelled from saline syringe 20 to purge air from tubing 46 and spike 48. Control 38 is then adjusted to place saline syringe 40 in fluid connection with dual check valve 50. A small volume of saline is expelled to purge flush bypass line 120 of air. Dual check valve 50 provides sufficient resistance to flow such that saline expelled from saline syringe 20 passes through bypass line 120 rather than through dual check valve 50.

Injector 70 is use to retract plunger 62 to draw saline from saline syringe 20. injector 70 is then used to expel air in line between syringe 60 and catheter 100 by expelling (via advancement of plunger 62) the saline therefrom. At this point, all lines of system 14 are free of air and filled with saline. Syringe 60 is substantially empty except for a small amount of saline not expelled.

At this point, injector syringe 60 is preferably positioned within dose calibrating unit 200 or other radiation containment device in the case of injection of a radiopharmaceutical. Container 44 is opened and pharmaceutical source 40 is spiked to place source 40 in fluid connection with valve system 16. Spiking of pharmaceutical source 40 can be done automatically, remotely or robotically to reduce or prevent exposure of operating personnel. The patient is then connected to patient fluid path set 80 via catheter 100. System 10 is now ready for an injection. The pharmaceutical is drawn into syringe 60 by retraction of plunger 62 relative to syringe tip 64 and then injected into the patient by advancement of plunger 62 relative to syringe tip 64. Saline is then expelled from saline syringe 20, passing through bypass line 120, to flush the pharmaceutical from patient fluid path set 80. All of these functions are accomplished with little on no exposure of the operator or administering personnel to radiation.

In that regard, all adjustment of control 38 were made before the radiopharrnaceutical was drawn into fluid delivery set 15. Control 38 can also be adjusted remotely or automatically (for example, via electronic/computer control) in, for example, cases when some pharmaceutical is within fluid delivery set 15 (for example, in a second or subsequent procedure in a case in which fluid delivery set 15 is used for multiple deliveries/injections) to prevent exposure of administering personnel. Other types of valve systems or assemblies, for example, a manifold system, can be used to effect the control of valve assembly 16.

Fluid delivery set 15 is preferably disposable after one or more uses to, for example, reduce the risk of cross-contamination between patients. Fluid delivery set 15, including valve system 16, and/or other components of system 10 can be placed within a protective containment unit 18 during use thereof to further shield personnel from radiation that may emanate from, for example, valve system 15. FIG. 1 B illustrates one embodiment of protective containment unit or shielded container 18 for fluid delivery set 15 of the present invention. In general, radioactive rays emanate in straight lines from a radiation source. Containment unit 18 provides a view of fluid delivery set 15 without providing a straight line of sight between the viewer and fluid delivery set 15. In that regard, it is often desirable for administering personnel to have a view of tubing in a fluid path to, for example, provide visual assurance of the absence of air bubbles. Containment unit 18 includes a shielded housing 160 having a view port 162. Radioactive frays cannot escape through view port 162 as there is no line of sight (that is, unobstructed line) between view port 162 and fluid delivery set 15. Containment unit 18 includes a mirrored surface 164 to provide a view of fluid delivery set 15. FIG. 1C illustrates another embodiment of a containment unit 18a in which a view of fluid delivery set 15 is provided by mirrored surface 174 which is in alignment with fluid delivery set 15 via view port 172. One or more additional mirrored surfaces 176 can be provided to give further views of fluid delivery set 15.

In each of containment units 18, one or more mirrored surfaces are used to provide a view of fluid delivery set 15 without creating an unshielded direct line between the viewer and the fluid delivery set 15 (or other radioactive source). There is no need to provide a transparent shield (for example, lead shielded glass) over view ports 162 or 172 because the lack of an unshielded direct line of sight between the viewer and fluid delivery set 15 prevents exposure to radiation. Elimination of leaded glass can be advantageous as such glass is often expensive and heavy and can sometimes diminish or degrade a view.

In the case of injection of a radiopharmaceutical, positioning a pressurizing unit or chamber such as syringe 60 within dose calibrating unit 200 such as the Capintec CRC-15PET dose calibrator available from Capintec, Inc. of Ramsey, N.J., which measures the total radiation of the volume of radiopharmaceutical enclosed within the pressurizing chamber, shields administering personnel from radiation and enables delivery of a known volume of the radiopharmaceutical having a known radiation level (as measured directly by dose calibrating unit 200). The accurate control of injection volume and flow rate provided by powered injector 70 enables automatic injection of a calculated volume of fluid (using for example processing unit 71 of injector 70) that will provide the level of radiation necessary, for example, for a PET or SPECT image given the measured radiation of the total volume of radiopharmaceutical contained within syringe 60 provided by dose calibration unit 200. Thus, it is no longer necessary to calculate and wait for the precise moment in time when radioactive decay has brought the level of radiation of a volume of radiopharmaceutical to the desired level, thereby saving time, and reducing the complexity of the injection procedure.

FIGS. 2–4C illustrate one embodiment of a setup for system 10 as described above. In this embodiment, a PULSAR injector available from Medrad, Inc. of Indianola, Pa. was used. Injection head 72 was separated from control unit 74 as described in U.S. Provisional Patent Application Ser. No. 60/167,309, filed Nov. 24, 1999, U.S. patent application Ser. No. 09/721,427 filed Nov. 22, 2000 and U.S. patent application Ser. No. 09/826,430 filed Apr. 3, 2001, all assigned to Medrad, Inc. Injection head 72 is slidably positioned in general alignment with an opening 204 in dose calibration unit 200 on a generally vertical slide bar or stand 220 via a clamping extension 224. Injector 70 also includes a first remote control unit 76 for communicating data/instructions such as injection volume and flow rate into control unit 74 remotely (via, far example, communication line 75). Further, injector 70 includes a second remote control unit 78 for remote manual control of drive member 79 of injector 70. The function of first remote control unit 76 and second control unit 78 can be combined. On currently available PULSAR injectors, manual controls for drive member 79 are positioned upon injector head 72. However, to prevent undesirable exposure to radiation in system 10 of the present invention, such controls are preferably also positioned remotely from injector head 72. Saline source/syringe 40 can also be controlled via injector 70 through a second injector head (not shown) as described, for example, in U.S. Provisional Patent Application Ser. No. 60/167,309, filed Nov. 24, 1999, U.S. patent application Ser. No. 09/721, 427 filed Nov. 22, 2000 and U.S. patent application Ser. No. 09/826,430 filed Apr. 3, 2001.

In the embodiment of FIGS. 2A through 4C, system 10 is positioned upon a cabinet stand 300. Slide bar 220 extends generally vertically from cabinet stand 300. Cabinet stand 300 includes a passage 310 farmed therein through which syringe 60 can pass to enter dose calibration unit 200. Cabinet stand 300 also preferably includes a second passage 320 through which pharmaceutical source 40 can pass to be deposited with container 44. A cap 330 can be provided to seal container 44. In the embodiment of FIGS. 2A through 4C, first passage 310 is preferably oriented such that radiation emanating therefrom is directed generally vertically toward the ceiling (or in another suitable direction) to reduce the likelihood that personnel within the room of the injection procedure will be exposed to such radiation.

Injector head 72 is oriented in a generally vertical, downward direction on slide bar 220 to position syringe 60 within dose calibrating unit 200. To ensure that air is purged from a syringe, however, injector heads are typically positioned such that the exit or syringe tip of the syringe if oriented upward during purging. As air is less dense than other injection media and saline flushes, the air rises to the syringe tip or exit and is readily purged by, for example, forcing a small amount of fluid from the syringe. To enable a generally vertical orientation of syringe 60 with syringe tip 64 oriented upward in the present invention, a syringe adapter 400 was used.

Syringe adapter 400 attaches to injector 70 in preferably the same manner as syringes are attached thereto. Attachment adapters can be used as known in the art to facilitate such attachment. Adapter 400 can, for example, be removably attached to injector 70 via flanges 412 on an attachment member 410 that cooperate with retaining slots in injector 70 (not shown) as described in U.S. Pat. No. 5,383,858, assigned to the assignee of the present invention, the disclosure of which is incorporated herein by reference.

Figure 4C:
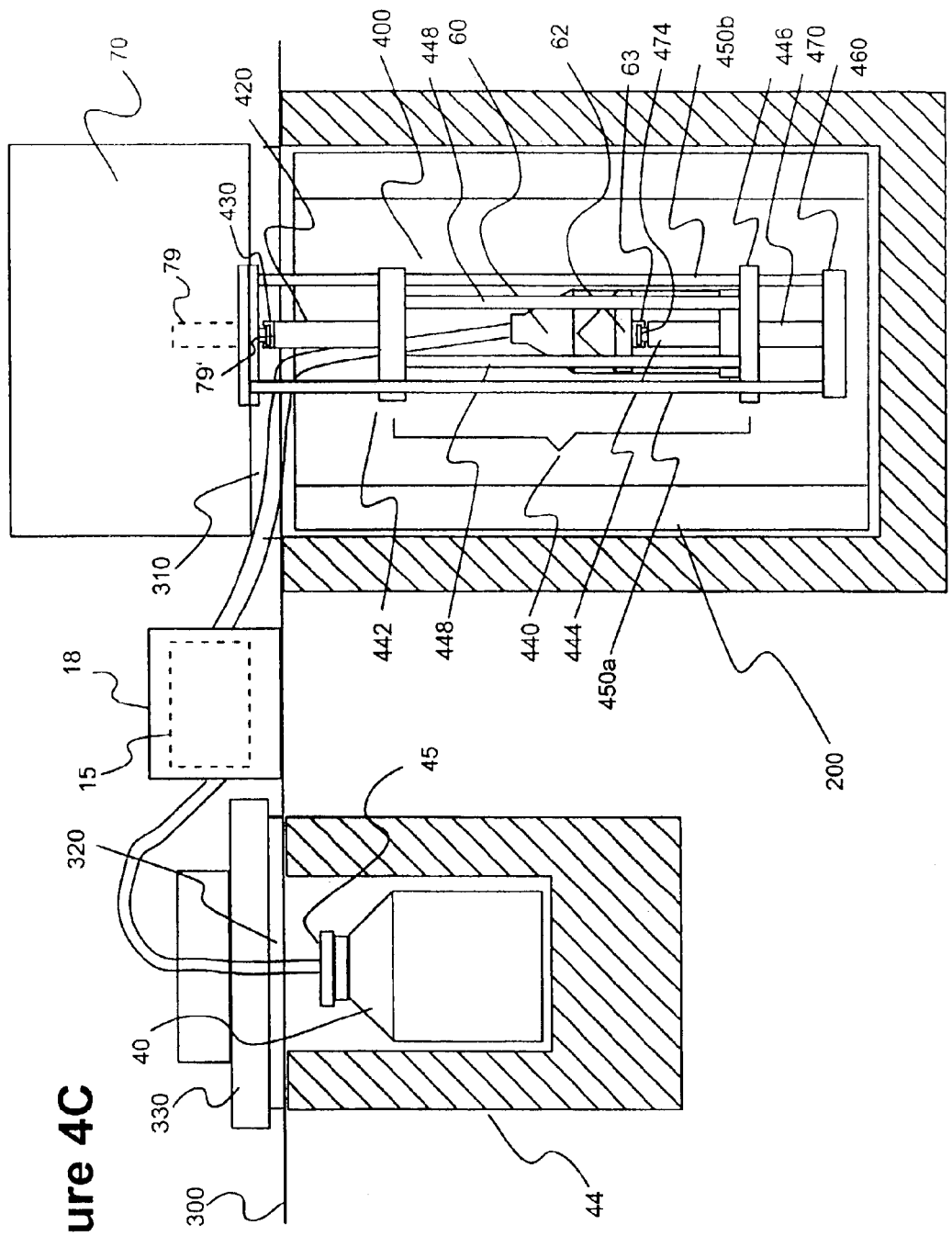
FIG. 4C illustrates a side cross-sectional view a portion of the system of FIGS. 1 through 4B.

Adapter 400 includes a drive extension 420 that removably connects to drive member 79 of injector 70 via an attachment member 430 that can, for example, include capture members that cooperate with a drive member flange 79. Drive extension 420 attaches to a syringe carriage 440 at an upper plate member 442 of syringe carriage 440. Syringe carriage 440 is slidable disposed upon adapter 400 via slide bars 450a and 450b that extend from the rear surface of attachment member 410 to a fixed, lower base 460. Syringe carriage 440 includes a syringe attachment member 444 attached to a lower plate member 446 of syringe carriage 440. Upper plate member 442 and lower plate member 446 are connected via connecting members 448 (for example, metal or plastic bars), Syringe attachment member 444 can include slots (not shown) that cooperate with flanges 66 on a rear portion of syringe 60 to removably attach syringe 60 to syringe carriage 444 as illustrated in FIGS. 4A, and 4C (as described, far example, in U.S. Pat. No. 5,383,858). Via syringe carriage 440, the barrel of syringe 60 is slidable in an upward and downward direction on adapter 400.

Adapter 400 further includes a plunger extension 470 that includes a plunger attachment including, for example, a flange 474 that cooperates with capture members 63 on the rear of plunger 62 to removably connect plunger extension 470 to plunger 62. Adapters as known in the art can facilitate connection of plunger extension 470 to various plungers. Plunger extension 470 maintains plunger 62 in a fixed position relative to base 460 and injector head 72. By upward and downward movement of syringe carriage 440 (via injector drive member 79 and drive extension 420), the position of plunger 62 within syringe 60 is changed. For example, advancing drive member 79 causes the barrel of syringe 60 to move downward and causes a corresponding or relative advancement of plunger 62 toward syringe tip 64, thereby causing fluid to be expelled from syringe 60. Upward movement (or retraction) of drive member 79 causes the barrel of syringe 60 to move upward and corresponds to retraction of plunger 62 relative to syringe tip 64, thereby drawing fluid into syringe 60.

An extending syringe adapter such as adapter 400, enables use of commercially available injector systems and commercially available dose calibrators in the system of the present invention without substantial modification. The use of adapter 400 is transparent to the injector control software/hardware as no change and/or recalibration of the controlled movement of drive member 79 of injector 70 is required.

Figure 5A:
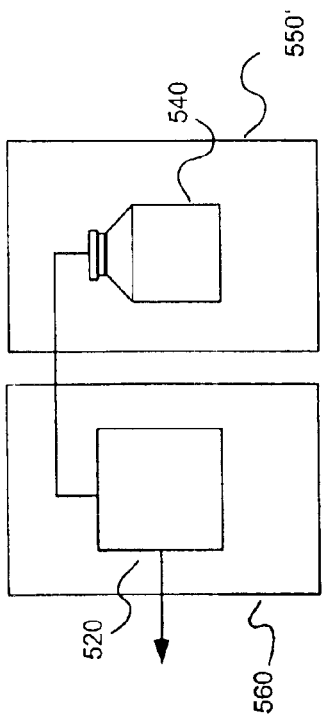
FIG. 5A illustrates a side cross-sectional view of an embodiment of the present invention in which dose calibration is provided by placing a pressurizing device and a source of radiopharmaceutical within a shielded dose calibrator.
Figure 5B:
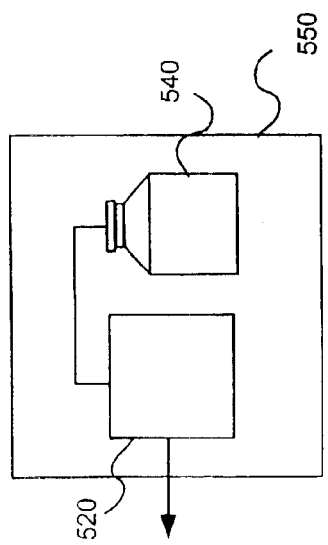
FIG. 5B illustrates a side cross-sectional view of an embodiment of the present invention in which dose calibration is provided by placing a source of radiopharmaceutical within a shielded dose calibrator.
Figure 5C:
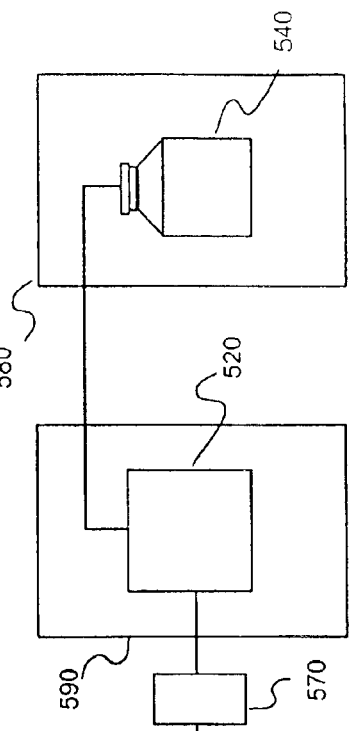
FIG. 5C illustrates a side cross-sectional view of an embodiment of the present invention in which dose calibration is provided by placing a radiation detector in line between a pressurizing device and a source of radiopharmaceutical within a shielded close calibrator.
Figure 5D:
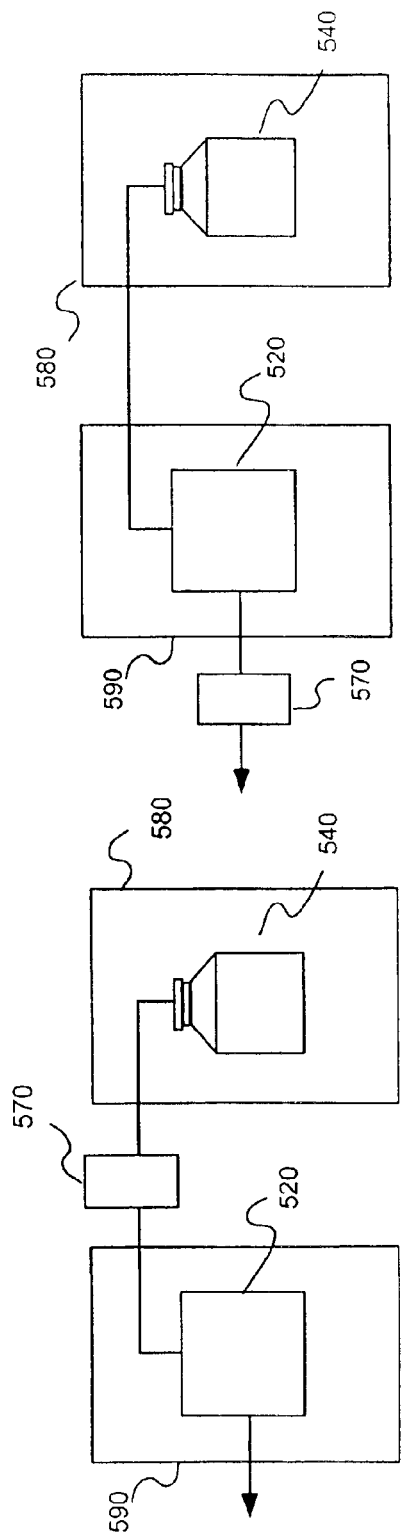
FIG. 5D illustrates a side cross-sectional view of an embodiment of the present invention in which dose calibration is provided by placing a radiation detector in line with the exit line of a pressurizing device.

FIGS. 5A Through 5D illustrate several other embodiments of the present invention for providing dose calibration generally in real time. In FIG. 5A, a pressurizing device 520 (for example, a syringe in communication with a powered injector) and a radiopharmaceutical source 540 are positioned within a dose calibrator 550. In FIG. 5B, radiopharmaceutical source 540 is placed in a dose calibrator 550', while pressurizing device 520 is placed in a shielded enclosure 560. In the embodiment of FIGS. 5C and 5D, radiation level detectors are placed in operative connection with flow lines (for example, tubing). In FIG. 5C, a radiation detector 570 is placed in line between radiopharmaceutical source 540 (enclosed within a shielded container 580) and pressurizing device 520 (enclosed within a shielded container 590). In FIG. 5D, a radiation detector 570' is placed in line with the exit of pressurizing device 540. In general, the flow rate through the line in operative connection with radiation detector 570 or 570' is known. The radiation level of a particular dose is thus easily measured using radiation detectors 570 and/or 570'.

Although the present invention has been described in detail in connection with the above examples, it is to be understood that such detail is solely for that purpose and that variations can be made by those skilled in the art without departing from the spirit of the invention except as it may be limited by the following claims.

We claim:

1. A shield for use with a radiopharmaceutical, the shield including a housing that is impenetrable by radioactive energy from the radiopharmaceutical, the shield also including at least one opening in the housing through which an article containing the radiopharmaceutical and positioned within the housing can be viewed, the opening being in visual alignment with a reflective surface in which a viewer can view a reflection of the article, the opening being positioned within the housing such that there is no direct line between the viewer and the article that is not shielded by a portion of the housing.

* * * * *